United States Patent [19]

Kline

[11] Patent Number: 4,991,124
[45] Date of Patent: Feb. 5, 1991

[54] SYSTEM AND METHOD FOR ULTRASONIC DETERMINATION OF DENSITY

[75] Inventor: Bruce R. Kline, Starksboro, Vt.

[73] Assignee: Simmonds Precision Products, Inc., Wilmington, Del.

[21] Appl. No.: 255,900

[22] Filed: Oct. 11, 1988

[51] Int. Cl.$^5$ .......................... G01N 9/00; G06F 15/52
[52] U.S. Cl. .................................... 364/558; 73/32 A; 73/579; 73/602; 73/628; 250/301
[58] Field of Search ................... 250/301; 364/558; 73/23, 24, 30, 32 R, 32 A, 584, 602, 596, 627, 628, 629, 579

[56] References Cited

U.S. PATENT DOCUMENTS

| | | | |
|---|---|---|---|
| 4,235,099 | 11/1980 | Ishizaka | 73/32 A |
| 4,297,608 | 10/1981 | Jensen | 310/335 |
| 4,364,273 | 12/1982 | Redding | 73/614 |
| 4,380,929 | 4/1983 | Taszarek et al. | 73/579 |
| 4,391,142 | 7/1983 | Cantrell, Jr. | 73/610 |
| 4,553,216 | 11/1985 | Stevens et al. | 364/558 |
| 4,566,330 | 1/1986 | Fujii et al. | 73/599 |
| 4,618,939 | 10/1986 | Davis | 364/558 |
| 4,630,482 | 12/1986 | Traina | 73/24 |
| 4,701,868 | 10/1987 | Regimand | 364/558 |

OTHER PUBLICATIONS

W. Sachse, "Density Determination of a Fluid Inclusion in an Elastic Solid from Ultrasonic Spectroscopy Measurements", 1974 Ultrasonics Symposium Proceedings, IEEE Cat. #74 CHO 896-ISU, pp. 716-719.

Primary Examiner—Parshotam S. Lall
Assistant Examiner—Brian M. Mattson
Attorney, Agent, or Firm—Dale R. Lovercheck

[57] ABSTRACT

A method and system determines the density of a liquid, such as aircraft fuel, by measuring the amplitude of the reflections of ultrasonic pulses from the faces of the walls of a reference material. A transducer is used to transmit an ultrasonic interrogation pulse through a liquid to the reference material. The density of the reference material is known, and its boundaries are well defined. The interrogation pulse is reflected from the faces of the reference material boundaries to provide first, second and third return pulses that can be used to determine the density of the liquid. The density determination is accomplished by determining characteristic impedances, reflection coefficients and transmission coefficients as a function of the returned pulse amplitudes.

18 Claims, 2 Drawing Sheets

SYSTEM AND METHOD FOR ULTRASONIC DETERMINATION OF DENSITY

The invention relates to a system and method of ultrasonic liquid fuel density determination. More particularly, the invention relates to ultrasonic density determination from the pulse amplitudes of three ultrasonic waves reflected from a reference material in a fuel tank.

The prior art is directed to the transmission of ultrasonic energy through various media and the analysis of return pulses (or echoes). The prior art does not provide a densitometer which uses three pulses which have traveled through different path lengths to determine the density of a liquid as is provided by the present invention.

Jensen, in U.S. Pat. No. 4,297,608 discloses an apparatus for ultrasonically determining the density of a liquid. In Jensen, an ultrasonic transducer transmits a pulse through a reference material that includes a reflective, discontinuous surface, through a region containing the liquid media, and to a reflector which provides a return echo through the media. The pulses returned from the surface of the reference material and the reflector are analyzed to determine the density of the fluid. Jensen requires a constant which must be experimentally determined during a calibration procedure. In the present invention, a third echo is used, and no calibration is needed.

Taszarek et al. in U.S. Pat. No. 4,380,929 discloses an ultrasound inspection apparatus for detecting flaws (e.g. cracks, voids, or other discontinuity) in a specimen. Ultrasonic energy is directed into a specimen which can include a flaw. A portion of the interrogation energy reverberates as a function of the resonant characteristics of the flaw with the return resonant energy analyzed with regard to wavelength to determine physical characteristics of the flaw. Taszarek et al. do not disclose a determination of density.

Redding in U.S. Pat. No. 4,364,273 discloses an apparatus for locating interfaces in a media, and in one embodiment, an ultrasonic transducer transmits energy to receivers to detect the presence of a dense layer in a tank of petroleum gas. Redding is involved with detection of inhomogeneities in a fuel measurement context and does not disclose density determinations.

Cantrell, Jr. et al. in U.S. Pat. No. 4,391,142 disclose a technique for ultrasonic analysis by which the sweep-frequency local oscillator of a spectrum analyzer drives an ultrasonic transducer to transmit a frequency-carrying interrogation pulse into a sample.

Fujii et al. in U.S. Pat. No. 4,566,330 disclose an apparatus and method specifically intended for use in an ultrasound medical apparatus and presents calibration arrangements which include a container of a standard fluid (degassed water) and a reflector. A transmitter emits a multi-frequency interrogation pulse with the reflected echoes analyzed to provide an attenuation coefficient. While Fujii et al. show the transmission of an interrogation pulse and analysis of the return pulses, Fujii et al. are concerned with the determination of attenuation coefficients rather than the density of the intervening fluid, as is provided by the present invention.

Sachse, *Density Determination of a Fluid Inclusion in an Elastic Solid From Ultrasonic Spectroscopy Measurements* 1974 Ultrasonics Symposium Proceedings, IEEE Cat. #74 CHO 896-ISU, pp 716–719, discloses an ultrasonic method by which the density of a fluid contained in a cylindrical cavity in an elastic solid is determined.

BRIEF DESCRIPTION OF THE INVENTION

A method and system determines the density of a liquid, such as aircraft fuel, by measuring the amplitude of the reflections of an ultrasonic pulse from the faces of the walls of a reference material. The densitometer system uses a transducer to transmit ultrasonic interrogation pulses through an evaluation material, such as a liquid fuel, to a reference material having a known density and well-defined boundaries, such as a glass, magnesium or aluminum block. The reference material has a pair of flat parallel sides, the planes of which are about perpendicular to the line of travel of the pulses to the center of each side.

The interrogation pulse is reflected from the flat sides of the reference material to provide first, second and third return pulses that can be used to determine the density of the evaluation material. The first return pulse is reflected from the outer face of the near side of the reference material, the second return pulse is reflected from the inner face of the far side of the reference material, and the third return pulse is the remnant of the second return pulse which is reflected from the inner near face of the rear side of the reference material and a second time from the inner face of the far side of the reference material. The density is determined as a function of the amplitudes of the return pulses.

DETAILED DESCRIPTION OF THE INVENTION

Figure 1:
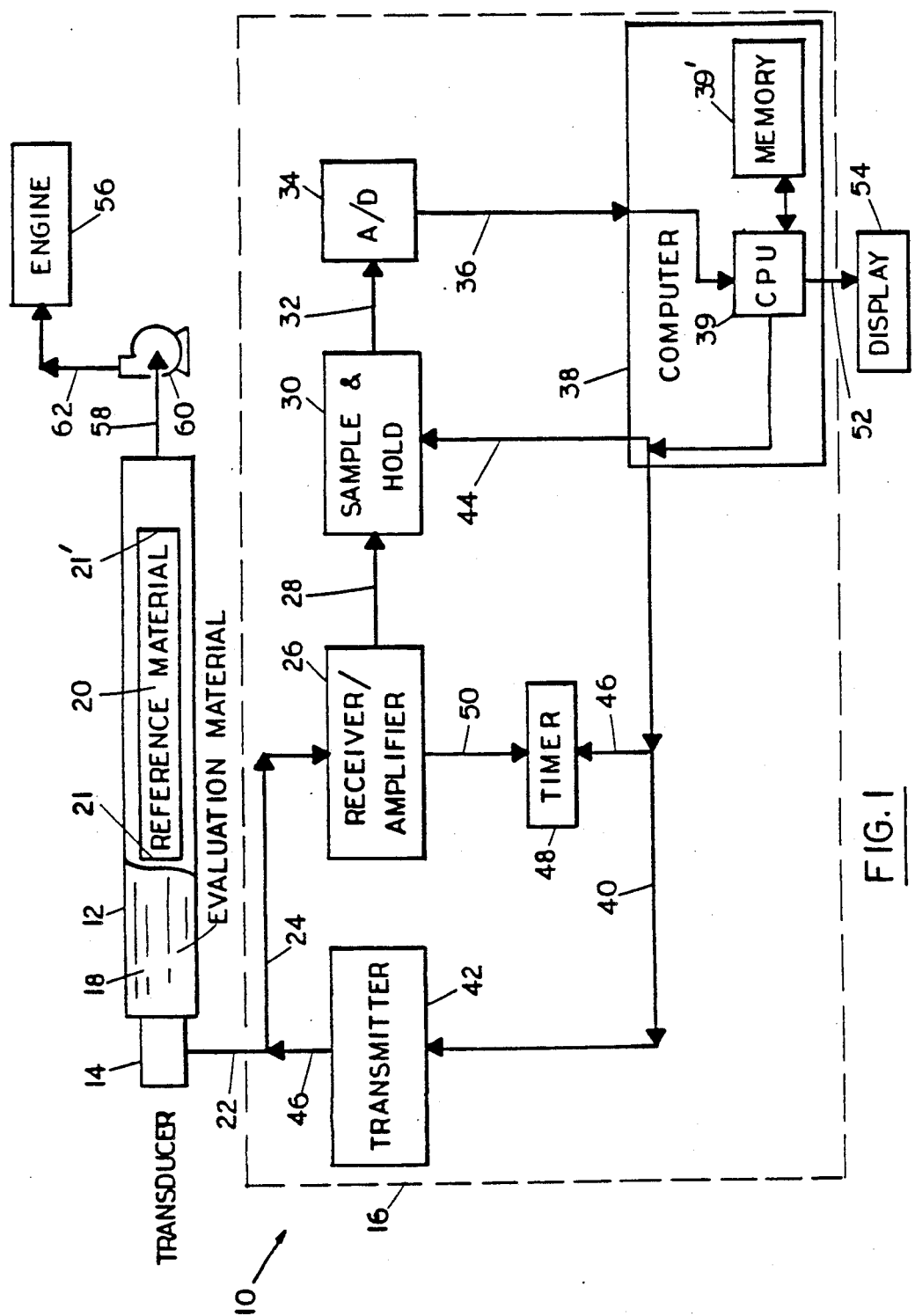
FIG. 1 is a schematic representation of an ultrasonic density measurement system in accordance with the invention.

The invention is now described in more detail with reference to the drawings. With more particular reference to FIG. 1, an ultrasonic density measurement system 10 is shown in accordance with the invention. The density measurement system 10 includes a container 12, ultrasonic transducer 14 and monitoring circuit 16. The transducer 14 is connected to the container 12 and to the monitoring circuit 16. The container 12 encloses evaluation material 18, such as liquid aircraft fuel, and reference material 20. The reference material 20 preferably is glass, aluminum or magnesium. Most preferably the reference material is glass. Transducer 14 is connected through electrical conductors 22 and 24 to receiver/amplifier 26. Receiver/amplifier 26 receives and amplifies signals from transducer 14 and sends amplified signals through electrical conductor 28 to sample and hold 30, which is connected by electrical conductor 32 to analog to digital converter (A/D) 34. Converter 34 sends digital signals through electrical conductor 36 to computer 38. Computer 38 sends signals through electrical conductor 40 to transmitter 42, through electrical conductor 46 to timer 48 and through electrical conductor 44 to sample and hold 30. The transmitter 42 is connected through electrical conductor 46 to transducer 14. The computer 38 is connected through electrical conductor 52 to display 54. Computer 38 includes a central processing unit (CPU) 39 (which preferably is a microprocessor) which is connected to memory 39'. Evaluation material 18, such as liquid fuel, from container 12 is pumped to engine 56 through line 58 by pump 60, which is connected by line 62 by engine 56. Engine 56 is preferably a jet or turbine combustion engine.

Figure 2:
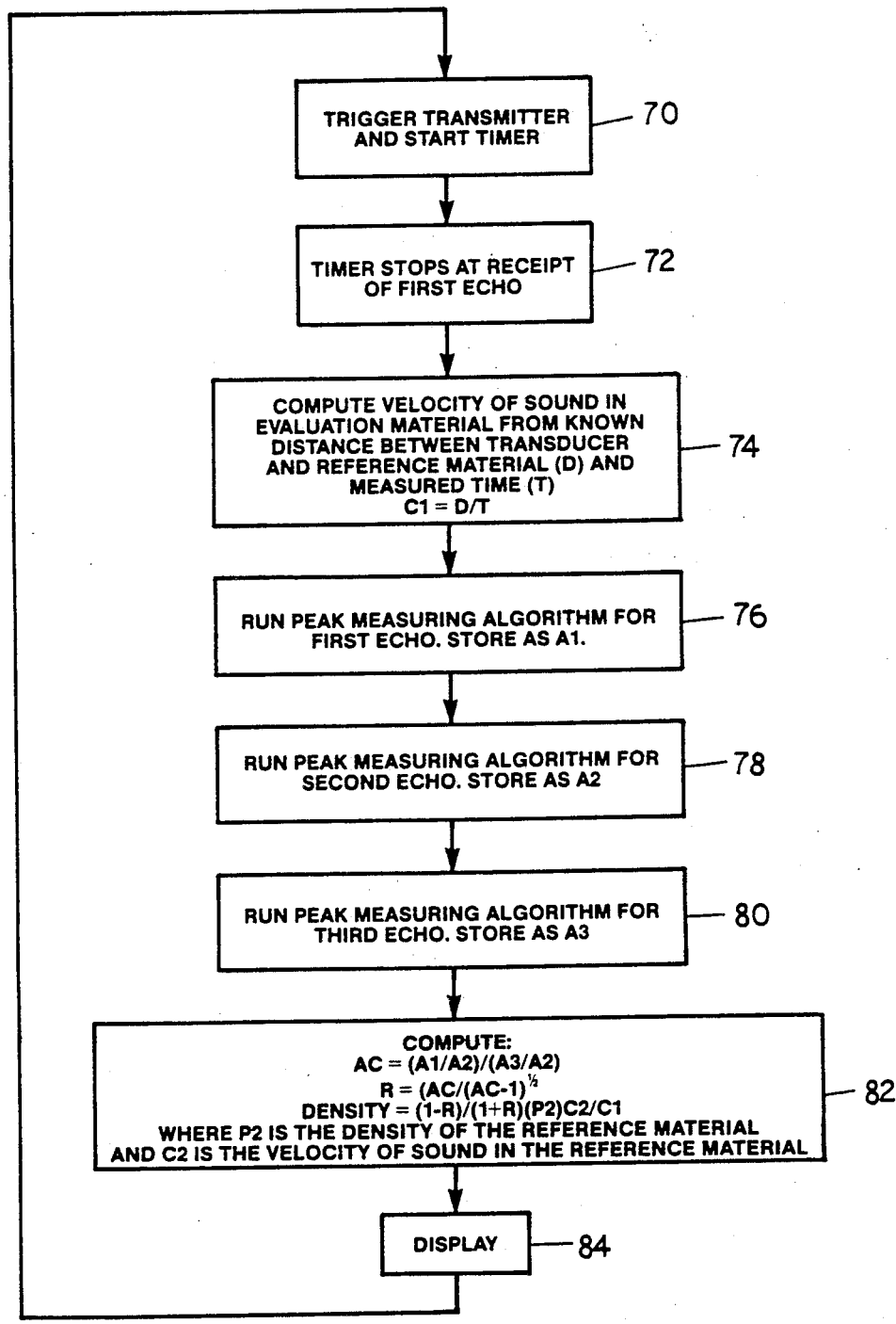
FIG. 2 is a schematic representation of the logical steps stored in memory and carried out in the microprocessor of the computer of an ultrasonic density measurement system in accordance with the invention.

With more particular reference to FIG. 2, a flowchart of the operations of the computer 38 is shown. The computer 38 triggers the transmitter 42 to signal the transducer 14 to transmit ultrasonic waves into the evaluation material 18. The waves travel the distance from the transducer 14 through the evaluation material 18 to the reference material 20 and are partially reflected therefrom back to the transducer 14 in time period (T). The velocity of sound in evaluation material 18 is determined from the relationship that the velocity of sound in the evaluation material (C1) is equal to the distance traveled (D) divided by the time (T) required for an ultrasonic wave to travel the known distance (D) from the transducer 14 to face 21 of the reference material and back to transducer 14, (i.e. C1=D/T) as noted in FIG. 2.

Upon arrival at transducer 14 of the wave (pulse or echo) reflected from the outer face of side 21 of the reference material 20 nearest to the transducer, the transducer 14 sends a signal to receiver/amplifier 26 which sends a signal to timer 48 through electrical conductor 50. The time for the ultrasonic pulse to travel from the transducer to the reference material 20 and the first reflection (return pulse or echo) to travel back to the transducer 14 is stored by the computer 38 for use in determining the velocity of sound in the evaluation material 18. The amplitude of the first reflection from the evaluation material 18 is determined in central processing unit (CPU) 39 and stored in memory 39' as A1. The wave reflected once from the inner face of the far side 21' is the second reflection (return pulse or echo), and its amplitude is determined in the central processing unit (CPU) 39 and stored in memory 39' as A2. The amplitude of the wave reflected twice from the inner face of the far side 21' is the third reflection (return pulse or echo), and its amplitude is determined in the central processing unit (CPU) 39 and stored in memory 39'. The density of the evaluation material 18 is determined by the central processing unit 39 and displayed on display 54. The dimensions of the monitored portion of the evaluation material and reference material should be large enough so that the three echoes do not overlap or otherwise interfere with each other. For example, the known material may be six inches in length, six inches in width and six inches in depth. Preferably, the length, width and depth of the reference material are each from about one to twelve inches. Larger dimensions than these for the reference material, while operable, would represent undesirable added weight that the aircraft would be required to carry. Preferably, the monitored portion of the evaluation material has dimensions of length, width and depth which are at least as large as the range(s) preferred for the reference material 20. The "length" of the monitored portion of the evaluation material is the distance from the wall of the container at or adjacent to the transducer 14 to the face 21 which is the face of the reference material 20, which is closest to the transducer. Preferably, the height of the monitored portion of the evaluation material 18 in the container 12 is sufficient to cover the reference material 20. Thus, the reference material is preferably located in the lower portion of the container.

Density of the evaluation material 18 may be determined in central processing unit 39 using information and relationships stored in memory 39' including Equation (I) as follows:

$$P1 = [(1-R)/(1+R)] \, (P2) \, C2/C1 \tag{I}$$

wherein P1 is the density of the evaluation material 18, P2 is the density of the reference material 20, C1 is the velocity of sound in the evaluation material 18, C2 is the velocity of sound in the reference material 20 and R is the reflectivity (reflection coefficient) of the interfaces 21 and 21' between the reference material 20 and the evaluation material 18.

Reference material 20 includes faces 21 and 21' which are substantially equally polished (to reflect ultrasonic waves substantially equally). The planes of faces 21 and 21' are substantially parallel to each other and substantially perpendicular to the line of travel of the pulses from transducer 14 to center of face 21 of reference material 20. The reflectivity of interfaces 21 and 21' may be determined from Equation II as follows:

$$R = (AC/(AC-1))^{\frac{1}{2}} \tag{II}$$

wherein R is the reflectivity of the reference material 20, and AC may be determined from Equation III as follows:

$$AC = (A1/A2)*(A3/A2) \tag{III}$$

wherein A1 is the amplitude (or peak) of the first reflection (first echo, i.e the wave reflected from the outer face of the near side 21 of the reference material 20 nearest to the transducer 14), A2 is the amplitude (or peak) of the second reflection (second echo, i.e. the wave reflected once from the inner face of the far side 21' of the reference material 20), and A3 is the amplitude (or peak) of the third reflection (third echo, i.e. the wave reflected twice from the inner face of the far side 21' of the reference material 20).

Equation II is obtained by solving for the reflectivity, R in Equations IV, V, and VI:

$$A1 = A0 \, R \, e^{(-a1)(2d)} \tag{IV}$$

wherein A0 is the initial pulse amplitude, R is the reflectivity of the face 21, a1 is the attenuation coefficient of the evaluation material, 2d is the path length traveled by the first reflection which has an amplitude A1 and is reflected from face 21 of the reference material.

$$A2 = A0(1+R) \, (-R) \, (1-R) \, e^{(-a1)(2d)} \, e^{(-a2)(2a)} \tag{V}$$

wherein $(1+R)$ is the transmissivity from the evaluation material to the reference material, $(-R)$ is the reflectivity of the face 21', $(1-R)$ is the transmissivity from the reference material to the evaluation material, a2 is the attenuation coefficient of the reference material, and 2a is the path length in the reference material of the second reflection, which has an amplitude A2, and is reflected from face 21'.

$$A3 = A0(1+R) \, (-R)^3 \, (1-R) \, e^{(-a1)(2d)} \, e^{(-a2)(4a)} \tag{VI}$$

wherein $(-R)^3$ represents the three reflections in the reference material, and 4a is the path length in the reference material of the third reflection, which has an amplitude A3, and is reflected twice from face 21'.

The evaluation material is preferably liquid aircraft fuel. During operation of the engine 56 the fuel is pumped through fuel line 58 by pump 60, and through fuel line 62 into engine 56.

With more particular reference to FIG. 2, the logical steps carried out by computer 39 are shown. The sequence of steps begins with box 70 which indicates triggering the transmitter to start the timer. The timer stops at receipt of the first echo as indicated in box 72. Then, as shown in box 74, the velocity of sound in the evaluation material is computed. The amplitude peaks are measured to obtain A1, A2 and A3 as indicated by boxes 76, 78 and 80 respectively. The density of the evaluation material is then determined and displayed as indicated in boxes 82 and 84 respectively.

Thus, what has been described is a system and method for ultrasonic determination of density of liquid from the amplitude of reflections from the faces of a reference. While the invention has been described in connection with what is presently considered to be the most practical and preferred embodiments, it is to be understood that this invention is not limited to the disclosed embodiment, but, on the contrary, is intended to cover various modifications and equivalent arrangements included within the spirit and scope of the appended claims. It is to be understood that all such equivalent structures are to be included within the scope of the following claims.

What is claimed is:

1. A method of density determination for a material, comprising:
    supporting a liquid evaluation material and a reference material, said reference material having a first and a second reflecting face, said evaluation material having a density,
    transmitting an interrogation ultrasonic wave through said evaluation material and to said reference material,
    a first portion of said interrogation wave being reflected once from said first reflecting face to form a first reflected wave having a first amplitude,
    a second portion of said interrogation wave being reflected once from said second reflecting face to form a second reflected wave having a second amplitude,
    a third portion of said interrogation wave being reflected twice from said second reflecting face to form a third reflected wave having a third amplitude,
    measuring said first amplitude of said first reflected wave,
    measuring said second amplitude of said second reflected wave,
    measuring said third amplitude of said third reflected wave,
    determining said density of said evaluation material.

2. The method claim 1 wherein said evaluation material comprises liquid aircraft fuel.

3. The method of claim 1 wherein said reference material comprises glass.

4. The method of claim 1 further comprising supporting a computer and an ultrasonic transducer, said computer comprising a memory and a central processing unit, said computer being connected to said transducer.

5. The method of claim 4 wherein said central processing unit performs said determination of the density of said evaluation material from said first, second and third amplitudes.

6. The method of claim 5 wherein said density of said evaluation material is determined from a velocity of sound in said reference material.

7. The method of claim 6 wherein said density of said evaluation material is determined from a reflectivity of sound from said first and second faces of said reference material.

8. The method of claim 7 wherein said data for the density, the velocity of sound and reflectively in said reference material are stored in said memory.

9. The method of claim 1 wherein said first and said second face are coplanar.

10. The method of claim 1 wherein said evaluation material comprises liquid fuel and said reference material comprises magnesium.

11. The method of claim 1 wherein said reference material comprises aluminum.

12. The method of claim 1 wherein said reference material comprises two sides, each said side having a planar outer face, and the planes of each said outer face being parallel.

13. The method of claim 12 wherein each said face reflects ultrasonic waves equally.

14. The method of claim 1 wherein said reference material comprises aluminum.

15. A system for determining density, comprising:
    a computer,
    an ultrasonic transducer means,
    a fuel tank,
    a reference material, and
    liquid fuel,
    said computer being connected to said transducer, said transducer being connected to said tank, said tank enclosing said reference material and said liquid fuel, said computer comprising a memory and a central processing unit, said computer being connected to said transducer, said reference material having a first sound wave reflective planar side and a second sound wave reflective planar side, the plane of each of said sides being parallel, said first side comprising a forward face and a reverse face, said second side comprising a forward face, said transducer being positioned to transmit interrogation sound waves through said liquid fuel, each said face of said reference material, said reference material being positioned to reflect said interrogation sound waves to provide first, second and third reflected sound waves having a first, second and third amplitude, whereby said first, second and third reflected sound waves are detected by said transducer means, and said transducer being adapted to send signals representative of said first, second and third amplitudes to said computer to determine the density of said liquid fuel.

16. The system of claim 15 wherein said reference material comprises glass.

17. The system of claim 15 wherein said liquid fuel is aircraft fuel.

18. The system of claim 17 further comprising providing an aircraft engine, said engine being connected to said fuel tank.

* * * * *